United States Patent [19]

Volodarsky et al.

[11] Patent Number: 5,849,929
[45] Date of Patent: Dec. 15, 1998

[54] PROCESS FOR THE PREPARATION OF IMIDAZOLINE NITROXYL

[75] Inventors: Leonid B. Volodarsky, Novosibirsk, Russian Federation; Stephen M. Fagan, Newtonville, Mass.

[73] Assignee: Uniroyal Chemical Company, Inc., Middlebury, Conn.

[21] Appl. No.: 938,895

[22] Filed: Sep. 26, 1997

[51] Int. Cl.⁶ ...................... C07D 233/04; C07D 233/06; C07D 233/08
[52] U.S. Cl. .......................................... 548/347.1
[58] Field of Search ........................................... 548/347.1

[56] References Cited

U.S. PATENT DOCUMENTS

| | | | |
|---|---|---|---|
| 3,047,579 | 7/1962 | Witman | 548/347.1 |
| 3,732,244 | 5/1973 | Boocock | 548/347.1 |
| 3,799,942 | 3/1974 | Boocock et al. | 548/347.1 |
| 4,665,185 | 5/1987 | Winter et al. | 546/184 |
| 4,945,166 | 7/1990 | Baus et al. | 548/369 |

FOREIGN PATENT DOCUMENTS

| | | | |
|---|---|---|---|
| 567827 | 11/1993 | European Pat. Off. | 548/373.1 |
| 628563 | 12/1994 | European Pat. Off. | 548/372.1 |
| 1069635 | 11/1959 | Germany | 548/347.1 |
| 282330 | 9/1970 | U.S.S.R. | 548/347.1 |

*Primary Examiner*—Floyd D. Higel
*Attorney, Agent, or Firm*—Raymond D. Thompson

[57] ABSTRACT

A process is provided for the preparation of imidazoline derivatives such as imidazoline nitroxyls and 1-hydroxy imidazoline.

30 Claims, No Drawings

PROCESS FOR THE PREPARATION OF IMIDAZOLINE NITROXYL

BACKGROUND OF THE INVENTION

This invention relates to a process for the preparation of imidazoline derivatives, e.g., an imidazoline hydrate nitroxyl such as 2,2,4,5,5,-pentamethyl-3-imidazoline-1-oxyl (PMIO), a known polymerization inhibitor.

The oxidation of secondary amines to provide the corresponding nitroxyls can be accomplished by the use of aqueous hydrogen peroxide in the presence of perwolframate ion (O. L. Lebedev, et al. Doklady Akad. Nauk. SSSR 140, 1327 (1961); and O. L. Lebedev, et al., CA, 56,15479f (1962)). U.S. Pat. No. 4,665,185 describes the preparation of nitroxyl compounds possessing 5- or 6- membered rings in which a sterically hindered cyclic amine in an inert solvent is oxidized with a hydroperoxide in the presence of, as catalyst, a metal carbonyl, metal oxide, metal acetylacetonate or metal alkoxide of a Group IVb, Vb, VIb, VIIb, or VIII metal.

As disclosed by Volodarsky et al., "Synthesis and Reactions of α-Hydroxylamino-oximes", Synthesis No. 9, pp. 704–715 (1986), heterocyclic N-oxides and imidazoline nitroxides are prepared by the following five-step process:

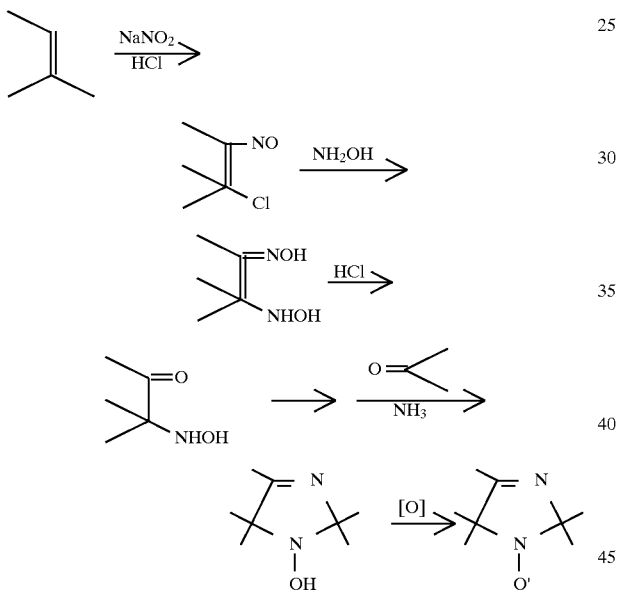

The nitroxides are prepared by first reacting an alkene with sodium nitrate and hydrochloric acid to produce a dimeric nitrosochloride. The dimeric nitrosochloride is then reacted with a hydroxylamine to provide an α-hydroxylamino-oxime which subsequently undergoes acid hydrolysis to the α-hydroxylaminoketone. The α-hydroxylaminoketone is then reacted with ammonia and ketone to provide a 1-hydroxy-3-imidazoline derivative which can be oxidized imidazoline nitroxide.

Given the relative expense of the hydroxylamine reactant used in the Voldarsky et al. synthesis, it would be advantageous to prepare an imidazoline nitroxyl by a synthetic route that avoids the use of hydroxylamine. It would also be desirable to produce an imidazoline nitroxyl employing a process that is simpler than the Volodarsky et al. process.

SUMMARY OF THE INVENTION

In accordance with the present invention, a process is provided for the preparation of an imidazoline nitroxyl which comprises:

a) reacting a haloketone with aqueous ammonia and a carbonyl compound, either simultaneously or sequentially, to provide an imidazoline hydrate;

b) recovering the imidazoline hydrate in substantially pure form;

c) dissolving the recovered imidazoline hydrate in an aqueous medium; and, d) oxidizing the dissolved imidazoline hydrate to provide an imidazoline nitroxyl.

The process of this invention provides a more economical procedure for preparing an imidazoline nitroxyl than the five-step process described in Volodarsky et al., supra.

DESCRIPTION OF THE PREFERRED EMBODIMENTS

The starting haloketone is preferably one conforming to the general formula

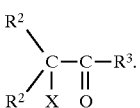

wherein $R^1$, $R^2$ and $R^3$, which may be the same or different, are hydrogen or alkyl, aryl, cycloalkyl, alkaryl, aralkyl or heterocyclic, or substituted derivative thereof, any two of $R^1$, $R^2$ and $R^3$ can be joined together to form a cyclic moiety, and X is halogen, it being provided that at least one of $R^1$ and $R^2$ is other than hydrogen. Useful haloketones include 3-chloro-3-methyl-2-butanone, 3-chloro-3-methyl-2-pentanone, 3-chloro-3-methyl-2-hexanone, 3-chloro-3-methyl-2-heptanone, 3-bromo-3-methyl-2-butanone, 3-bromo-3-methyl-2-pentanone, 3-bromo-3-methyl-2-hexanone, 3-bromo-3-methyl-2-heptanone, and the like. Of the foregoing haloketones, 3-chloro-3-methyl-2-butanone is preferred.

The selected haloketone is reacted with aqueous ammonia to produce an aminoketone as a transient intermediate. This intermediate reacts with additional aqueous ammonia to provide an aminoimine of the general formula

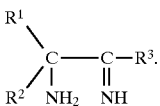

wherein $R^1$, $R^2$ and $R^3$ have the aforestated meanings.

The reaction of haloketone with aqueous ammonia is ordinarily carried out in the liquid phase employing a suitable solvent, e.g., an alcohol such as ethanol, methanol, propanol, t-butanol, t-pentanol, t-hexanol, t-octanol, isopropanol, and the like. The reaction is advantageously conducted at ambient temperature and pressure although elevated temperatures and pressures can also be utilized if desired. The molar ratio of aqueous ammonia to haloketone can ordinarily range from about 3 molar excess to about 10 molar excess and preferably from about 3 molar excess to about 6 molar excess.

The foregoing aminoimine is reacted with a carbonyl compound of the general formula

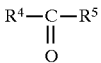

wherein $R^4$ and $R^5$, which may be the same or different, are hydrogen or alkyl, aryl, cycloalkyl, alkaryl, aralkyl or heterocyclic, or substituted derivative thereof, it being provided that at least one of $R^4$ and $R^5$ is other than hydrogen, or $R^4$ and $R^5$ can be joined together to form a cyclic moiety. Useful carbonyl compounds to react with the aminoimine include ketones such as acetone, methyl ethyl ketone, cyclopentanone, cyclohexanone, and the like and aldehydes such as formaldehyde, acetaldehyde propionaldehyde, butyraldehyde, and the like. Of the foregoing compounds, acetone is preferred.

The reaction is advantageously carried out at ambient temperature and pressure although elevated temperatures and pressures can also be utilized if desired. The molar ratio of the carbonyl compound to aminoimine can ordinarily range from about 2 molar excess to about 10 molar excess and preferably from about 2 molar excess to about 6 molar excess.

The reaction of the aminoimine with the carbonyl compound effects ring closure to provide an imidazoline hydrate in which the imidazoline conforms to the structure:

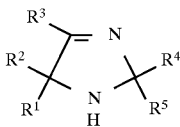

wherein $R^1$, $R^2$, $R^3$, $R^4$ and $R^5$ have the aforestated meanings.

The foregoing sequential reaction of haloketone with aqueous ammonia to provide an aminoimine intermediate compound and the reaction of the aminoimine with a carbonyl compound to provide an imidazoline hydrate can, if desired, be combined in a single step, i.e., the haloketone can be simultaneously reacted with the aqueous ammonia and the carbonyl compound to provide the hydrated imidazoline.

The imidazoline hydrate, whether formed by the aforementioned sequential or concurrent reactions, is recovered from the reaction medium as a solid employing any suitable procedure, e.g., centrifugation followed by decantation, filtration, and the like, to provide an imidazoline hydrate from which contaminates, including those that might reduce the yield of the subsequently produced imidazoline nitroxyl, have to a large extent been removed. The recovered imidazoline hydrate may be rinsed with acetone to increase its yield and to remove additional amounts of contaminates if present.

The recovered imidazoline hydrate is then dissolved in an aqueous medium such as water or alcohol and oxidized to provide product imidazoline nitroxyl of the general formula

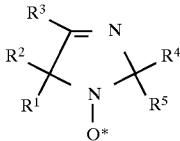

wherein $R^1$, $R^2$, $R^3$, $R^4$ and $R^5$ have the aforestated meanings.

Oxidation can be carried out by any known and conventional procedure, e.g., by means of a peroxide. Useful peroxides include hydrogen peroxide and hydroperoxides such as tert-butyl hydroperoxide, tert-amyl hydroperoxide, tert-hexyl hydroperoxide, tert-octyl hydroperoxide, ethylbenzene hydroperoxide, and the like with hydrogen peroxide being preferred. The amount of peroxide employed will ordinarily be that which is required to achieve essentially complete oxidation of the recovered imidazoline hydrate to produce imidazoline nitroxyl. In general, the peroxide:recovered imidazoline hydrate molar ratio can range from about 10:1 to about 5:1 and preferably from about 5:1 to about 1:1.

The oxidation of the recovered imidazoline hydrate with peroxide can be carried out in the presence of a metal-containing oxidation catalyst. The metal-containing oxidation catalyst is selected from among the metal carbonyls, metal oxides, metal acetylacetonates and metal alkoxides of a metal from Group IVb, Vb, VIb, VIb, and VIII of the periodic table. Examples of suitable catalysts include vanadyl acetylacetonate, cobalt carbonyl, titanium (IV) isopropoxide, molybdenum hexacarbonyl, molybdenum trioxide, sodium wolframate, and the like. Preferred catalysts are the alkali metal tungstates such as sodium tungstate.

The amount of catalyst which is added to the reaction mixture for oxidation purposes is not narrowly critical and need only be added in amounts effective to initiate the reaction. The preferred range of catalyst is from 0.001 mole percent or lower to about 0.01 mole percent or higher based upon the peroxide employed. Any amount can be used as long as it is catalytically effective. There is no limit to the upper range other than economic considerations.

It is also advantageous to include a chelating agent when oxidizing the recovered hydrated imidazoline. The chelating agent can be any known chelating agent capable of complying with the aforesaid catalytically active metal. A preferred chelating agent is ethylenediaminetetraacetic acid (EDTA). Useful amounts of chelating agent generally range from about 0.001 mole percent or lower to about 0.01 mole percent, or higher based upon solvent and peroxyed employed and preferably from about 0.001 mole percent to about 0.005 mole percent.

The temperature for the end product-forming reaction can range, e.g., from about 0° C. to about 100° C. and preferably at a temperature from about 20° C. to about 50° C. The reaction atmosphere for the end product-forming reaction can be ambient, oxygen enriched, or inert containing gases such as nitrogen, argon, and helium. At the end of the reaction, the imidazoline nitroxyl product is recovered employing any known and conventional procedure.

The foregoing imidazoline nitroxyls can be reduced to provide corresponding 1-hydroxy imidazolines of the general formula:

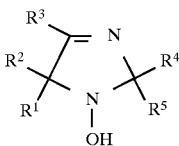

wherein $R^1$, $R^2$, $R^3$, $R^4$ and $R^5$ have the aforestated meanings. The reduction of the imidazoline nitroxyls to the 1-hydroxy imidazolines can be accomplished by catalytic hydrogenation employing a noble metal or nickel catalyst or by a reduction using zinc, borane, hydrazine hydrate or other conventional reducing agent. If desired, the 1-hydroxy imidazolines can be converted to the corresponding imidazoline nitroxyls employing a suitable oxidation procedure, e.g., the oxidation of the 1-hydroxy imidazolines with manganese oxide in ethyl acetate or ether.

The following examples illustrate the process of this invention.

EXAMPLE 1

This example illustrates the preparation of hydrated 2,2,4,5,5-pentamethyl-3-imidazoline hydrate.

A mixture of 120 g of 3-chloro-3-methyl-2-butanone and 300 ml of concentrated aqueous ammonia was stirred vigorously for 2 hours at ambient temperature. 600 ml of acetone was then added to the mixture until a clear homogenous solution was obtained. This solution was stored for 4–6 days until all the white precipitate had formed. The white precipitate having a light violet color was filtered, rinsed on the funnel with a small amount of cooled acetone and then dried on the filter. 95 g of slightly violet colored 2,2,4,5,5-pentamethyl-3-imidazoline hydrate was recovered with a yield of 60%.

EXAMPLE 2

This example illustrates another preparation of hydrated 2,2,4,5,5-pentamethyl-3-imidazoline hydrate.

To a solution of 60 g 3-chloro-3-methyl-2-butanone in 150 ml isopropanol, 150 ml concentrated aqueous ammonia was added. The clear solution was held for 2 hours at ambient temperature and treated with 500 ml acetone. The temperature was maintained at 30° C. and ammonia was bubbled through the solution for a period of 1 to 2 hours. The solution was stored for 2–4 days at ambient temperature until all the white precipitate had formed. The white precipitate was then filtered, rinsed on the funnel with a small amount of cooled acetone and dried on the filter. After storing in a refrigerator, the partially evaporated solution formed an additional amount of white precipitate. A total of 50 g of white 2,2,4,5,5-pentamethyl-3-imidazoline hydrate was recovered with a yield of 63%.

EXAMPLE 3

This example illustrates another preparation of hydrated 2,2,4,5,5-pentamethyl-3-imidazoline.

300 ml of acetone was saturated with ammonia at ambient temperature for a 1 hour period and treated with a solution of 150 ml 3-chloro-3-methyl-2-butanone in 150 ml acetone. The temperature of the solution was maintained at 30°–40° C. over an 8 hour period with 150 ml concentrated aqueous ammonia being added. The solution was stored for 2 days at ambient temperature and ample white precipitate was filtered and dried on the filter. 103 g of white 2,2,4,5,5-pentamethyl-3-imidazoline hydrate was recovered with a yield of 58%.

EXAMPLE 4

The example illustrates the preparation of 2,2,4,5,5-pentamethyl-3-imidazoline-1-oxyl.

3.1 g (0.02 mole) of white hydrate 2,2,4,5,5-pentamethyl-3-imidazoline prepared hydrate as described in any of Examples 1–3 supra was dissolved in 20 ml water containing 0.8 g (0.02 mole) NaOH, 0.27 g $Na_2WO_4$ and 0.27 g EDTA. This solution was oxidized with 5 ml of a 30% solution of $H_2O_2$ in water (g/g) added in 3 portions at ambient temperature. The reaction was slightly exothermic at ambient temperature and became more exothermic when the temperature was increased to 30° C. After 10–15 minutes, the temperature of the reaction mixture increased to 40°–50° C. and then decreased to ambient temperature over a half-hour period. The bright yellow solution was then saturated with $KHCO_3$ and extracted three times with 20 ml ether. The orange ether extracts were combined and dried over $MgSO_4$. Evaporation of ether yielded 1.2 g of 2,2,4,5,5-pentamethyl-3-imidazoline-1-oxyl as an orange oil.

EXAMPLE 5

This example illustrates another preparation of 2,2,4,5,5,-pentamethyl-3-imidazoline-1-oxyl.

63 g (0.4 mole) of white 2,2,4,5,5-pentamethyl-3-imidazoline hydrate prepared as described in any of Examples 1–3 was dissolved in 400 ml water containing 8.0 g (0.2 mole) NaOH, 2.7 g, $Na_2WO_4$ and 2.7 g EDTA. This solution was oxidized with 100 ml of a 30% solution of $H_2O_2$ in water (g/g) giving an exothermic reaction. The flask was cooled with current outer water and after 2 hours the aqueous layer was saturated with NaCl causing the organic phase to separate. The bright yellow organic phase was then extracted three times with small amounts of ether. After the extracts were dried with $MgSO_4$ and the combined organic layer extracts were evaporated, 36 g of 2,2,4,5,5-pentamethyl-3-imidazoline-1-oxyl was produced as an orange oil with a yield of 60%.

EXAMPLE 6

This example illustrates the preparation of 1-hydroxy-2,2,4,5,5-pentamethyl-3-imidazoline.

1.5 g (0.01 mole) of 2,2,4,5,5-pentamethyl-3-imidazoline-1-oxyl prepared as described in either of Examples 4 and 5 was solved in 10 ml methanol and treated with 1.5 ml (0.03 mole) of hydrazine or hydrazine-hydrate at ambient temperature. This solution was stored for 12 hours and over this period the methanol evaporated and the color of the solution disappeared. The partly crystallized residue was stirred with acetone and the colorless crystals were filtered and rinsed with acetone. 1.32 g of the isolated crystals with a yield of 88% were crystallized from ethyl acetate producing 1-hydroxy-2,2,4,5,5-pentamethyl-3-imidazoline having a melting point of 127°–128° C.

what is claimed is:

1. A process for the preparation of an imidazoline nitroxyl which comprises:

a) reacting a haloketone with aqueous ammonia and a carbonyl compound, either simultaneously or sequentially, to provide an imidazoline hydrate;

b) recovering the imidazoline hydrate in substantially pure form;

c) dissolving the recovered hydrated imidazoline in an aqueous medium; and, d) oxidizing the dissolved imidazoline hydrate to provide an imidazoline nitroxyl.

2. The process of claim 1 wherein in step (a) a haloketone of the formula

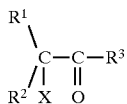

in which $R^1$, $R^2$ and $R^3$, which are the same or different, are hydrogen or alkyl, aryl, cycloalkyl, alkaryl, aralkyl or heterocyclic, and X is halogen, it being provided at least one of $R^1$ and $R^2$ is other than hydrogen, and any two of $R^1$, $R^2$ and $R^3$ optionally form a cyclic moiety, is sequentially or simultaneously reacted with aqueous ammonia and a carbonyl compound of the formula

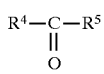

wherein $R^4$ and $R^5$, which are the same or different, are hydrogen or alkyl, aryl, cycloalkyl, alkaryl, aralkyl or heterocyclic, it being provided that at least one of $R^4$ and $R^5$ is other than hydrogen, or $R^4$ and $R^5$ optionally form a cyclic moiety, to provide an imidazoline hydrate in which the imidazoline is of the formula

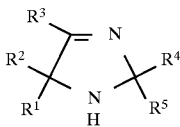

wherein $R^1$, $R^2$, $R^3$, $R^4$ and $R^5$ have the aforestated meanings and in step (d), the dissolved imidazoline hydrate is oxidized to provide the product imidazoline nitroxyl of the formula

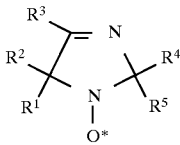

wherein $R^1$, $R^2$, $R^3$, $R^4$ and $R^5$ have the aforestated meanings.

3. The process of claim 2 wherein $R^1$, $R^2$, $R^3$, $R^4$ and $R^5$ are methyl.

4. The process of claim 2 wherein step (a) takes place within a solvent selected from the group consisting of ethanol, methanol, propanol, t-butanol, t-pentanol, t-hexanol, t-octanol, isopropanol and mixtures thereof.

5. The process of claim 2 wherein the carbonyl compound is acetone.

6. The process of claim 2 wherein oxidizing step (d) is carried out with a peroxide.

7. The process of claim 6 wherein the peroxide is hydrogen peroxide.

8. The process of claim 7 wherein the molar ratio of hydrogen peroxide:recovered hydrated imidazoline is not greater than about 10:1.

9. The process of claim 7 wherein the molar ratio of hydrogen peroxide:recovered imidazoline hydrate is not greater than about 5:1.

10. The process of claim 2 wherein oxidizing step (d) takes place in the presence of a catalyst.

11. The process of claim 10 wherein the catalyst is an alkali metal wolframate.

12. The process of claim 2 wherein oxidizing step (d) takes place in the presence of a chelating agent.

13. The process of claim 12 wherein the chelating agent is ethylene diaminetetraacetic acid.

14. The process of claim 2 wherein the reaction temperature of step (d) is from about 0° C. to about 100° C.

15. The process of claim 2 wherein the reaction temperature of step (d) is from about 20° C. to about 50° C.

16. The process of claim 2 which further comprises:
e) reducing the imidazoline nitroxyl to produce a 1-hydroxy imidazoline of the formula:

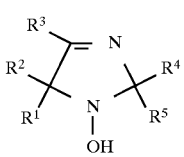

wherein $R^1$, $R^2$, $R^3$, $R^4$ and $R^5$, which are the same or different, are hydrogen or alkyl, aryl, cycloalkyl, alkaryl, aralkyl or heterocyclic, it being provided that at least one of $R^1$ and $R^2$ and at least one of $R^4$ and $R^5$ is other than hydrogen, and any two R groups on the same or adjacent carbon atoms optionally form a cyclic moiety.

17. The process of claim 16 wherein reducing step (e) is carried out with a reducing agent selected from the group consisting of zinc, borane, and hydrazine hydrate.

18. A process for the preparation of 2,2,4,5,5-pentamethyl-3-imidazoline-1-oxyl which comprises:

a) reacting 3-chloro-3-methyl-2-butanone with aqueous ammonia and acetone, either simultaneously or sequentially, to provide 2,2,4,5,5-pentamethyl-3-imidazoline hydrate;

b) recovering the 2,2,4,5,5-pentamethyl-3-imidazoline hydrate in substantially pure form;

c) dissolving the recovered 2,2,4,5,5-pentamethyl-3-imidazoline hydrate in an aqueous medium; and, d) oxidizing the dissolved 2,2,4,5,5-pentamethyl-3-imidazoline hydrate to provide product 2,2,4,5,5-pentamethyl-3-imidazoline-1-oxyl.

19. The process of claim 18 wherein step (a) is carried out in a solvent selected from the group consisting of ethanol, methanol, propanol, t-butanol, t-pentanol, t-hexanol, t-octanol, isopropanol and mixtures thereof.

20. The process of claim 18 wherein oxidizing step (d) is carried out with a peroxide.

21. The process of claim 20 wherein the peroxide is hydrogen peroxide.

22. The process of claim 21 wherein the molar ratio of hydrogen peroxide:2,2,4,5,5-pentamethyl-3-imidazoline hydrate is not greater than about 10:1.

23. The process of claim 21 wherein the molar ratio of hydrogen peroxide:2,2,4,5,5-pentamethyl-3-imidazoline hydrate is not greater than about 5:1.

24. The process of claim 18 wherein oxidizing step (d) takes place in the presence of a catalyst.

25. The process of claim 24 wherein the catalyst is an alkali metal wolframate.

26. The process of claim 24 wherein oxidizing step (d) takes place in the presence of a chelating agent.

27. The process of claim 26 wherein the chelating agent is ethylene diaminetetraacetic acid.

28. The process of claim 18 wherein the reaction temperature of step (d) is from about 0° C. to about 100° C.

29. The process of claim 18 wherein the reaction temperature of step (d) is from about 20° C. to about 50° C.

30. The process of claim 18 which further comprises the step of reducing 2,2,4,5,5-pentamethyl-3-imidazoline-1-oxyl to provide 1-hydroxy-2,2,4,5,5-pentamethyl-3-imidazoline.

* * * * *